United States Patent
Bowser et al.

(10) Patent No.: US 6,419,674 B1
(45) Date of Patent: *Jul. 16, 2002

(54) RADIO FREQUENCY DILATOR SHEATH

(75) Inventors: Donald J. Bowser, Vandergrift; Carl A. Cook, Monroeville; Louis B. Goode, Cranberry Township; William L. Johnson, Kittanning; Barry E. Norlander; James R. Zewe, both of Pittsburgh, all of PA (US)

(73) Assignee: Cook Vascular Incorporated, Leechburg, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,801

(22) Filed: Nov. 26, 1997

Related U.S. Application Data

(60) Provisional application No. 60/031,961, filed on Nov. 27, 1996, and provisional application No. 60/038,521, filed on Feb. 26, 1997.

(51) Int. Cl.[7] ............................................. A61B 17/39
(52) U.S. Cl. ............................ 606/45; 607/101; 606/49
(58) Field of Search ............................ 606/45, 48–50, 606/108, 101; 607/115, 116

(56) References Cited

U.S. PATENT DOCUMENTS

| | | |
|---|---|---|
| 4,936,281 A | 6/1990 | Stasz |
| 5,083,565 A | 1/1992 | Parins |
| RE33,925 E | 5/1992 | Bales et al. |

(List continued on next page.)

FOREIGN PATENT DOCUMENTS

| | | |
|---|---|---|
| EP | 0368568 | 5/1990 |
| EP | 0573334 | 5/1993 |
| WO | 9202272 | 2/1992 |
| WO | 9509575 | 4/1995 |
| WO | 9533513 | 12/1995 |

OTHER PUBLICATIONS

NASPE Abstracts, "Bipolar Electrosurgical Dissection Sheath for Lead Extraction: Design and Initial Feasibility," PACE, vol. 20, Section 317, Apr. 1997, Part II, p. 1129.

Harrington, Davie P., *EXAMplifications*, "Electrosurgery Fact and Fiction", Biomedical Instrumentation & Technology, Jul./Aug. 1994, pp. 331–333.

Tucker, Robert D. et al., *The Journal of Urology*, vol. 141, "A comparison of Urologic Application Of Bipolar Versus Monopolar Five French Electrosurgical Probes", Sep. 9, 1988, pp. 662–665.

(List continued on next page.)

*Primary Examiner*—Linda C. M. Dvorak
*Assistant Examiner*—Roy Gibson
(74) *Attorney, Agent, or Firm*—Charles W. Agnew; Richard J. Godlewski

(57) ABSTRACT

A medical device (10) such as a radio frequency dilator sheath for separating an encapsulated elongated structure (11) such as an electrical cardiac lead implanted in biological tissue (12) such as a vessel leading to or from a patient's heart. The radio frequency dilator sheath includes inner and outer coaxial dilator sheaths (13 and 28) with respective beveled distal ends (18 and 36) for mechanically loosening and separating encapsulating tissue from an implanted electric cardiac lead. The beveled distal end of the inner sheath is truncated to form a transverse face or surface (89) that is approximately perpendicular to the longitudinal axis of the sheath. Electrical conductors (16 and 17) are positioned about the distal end (14) and passage (15) of the inner dilator sheath. When energized, the electrical conductor emits an electrical arc which electrically separates encapsulating biological tissue from the elongated electrical structure implanted therein and placed in the passage of the inner elongated dilator sheath.

19 Claims, 10 Drawing Sheets

U.S. PATENT DOCUMENTS

| | | | |
|---|---|---|---|
| 5,277,696 A | * | 1/1994 | Hagen .......................... 606/49 |
| 5,423,806 A | | 6/1995 | Dale et al. |
| 5,500,012 A | * | 3/1996 | Brucker et al. ............. 607/122 |
| 5,507,751 A | | 4/1996 | Goode et al. |
| 5,624,439 A | * | 4/1997 | Edwards et al. ............... 606/45 |
| 5,651,781 A | * | 7/1997 | Grace ............................ 606/1 |
| 5,674,217 A | * | 10/1997 | Wahlstrom et al. ........... 606/15 |
| 5,749,914 A | * | 5/1998 | Janssen ...................... 607/116 |
| 5,779,715 A | * | 7/1998 | Tu ............................. 606/108 |
| 5,824,026 A | | 10/1998 | Diaz |
| 5,836,946 A | | 11/1998 | Diaz et al. |

OTHER PUBLICATIONS

Byrd, Charles L., "Management Of Implant Complications", 1995, Chap. 28, Clinical Cardiac Pacing, pp 491–522.

Spectranetics Sales Brochure, "Excimer Laser Angioplasty System", date unknown.

* cited by examiner

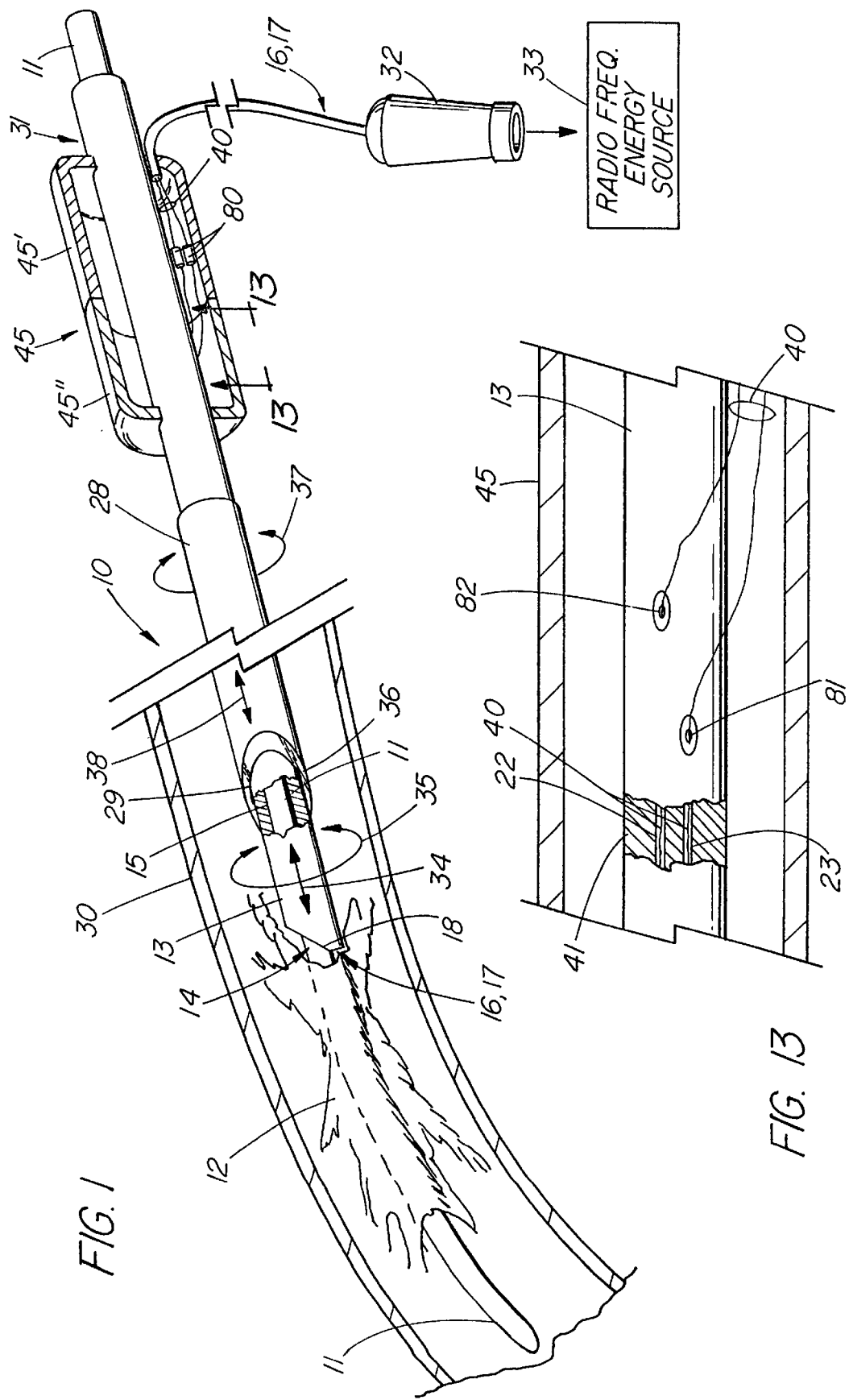

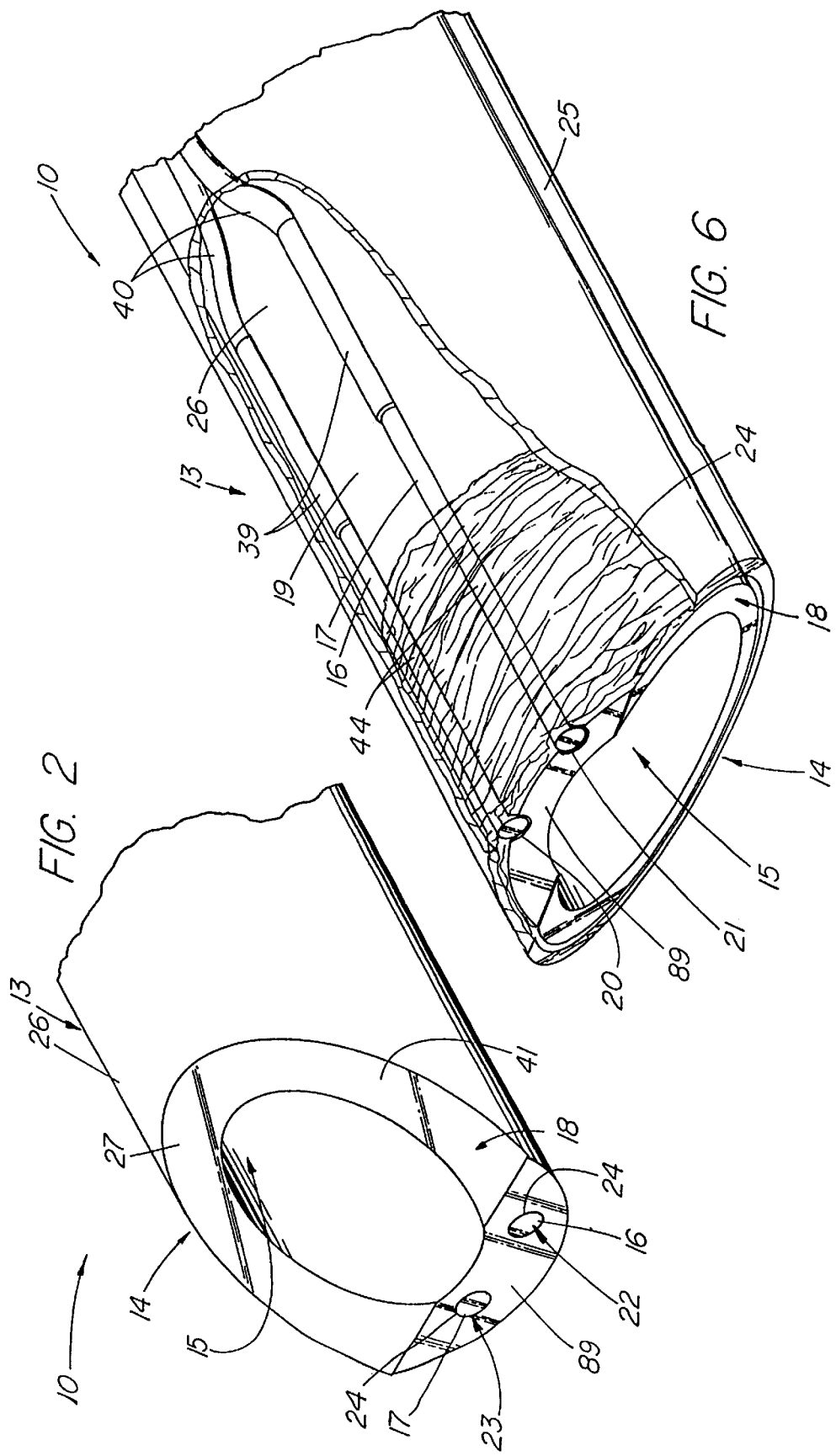

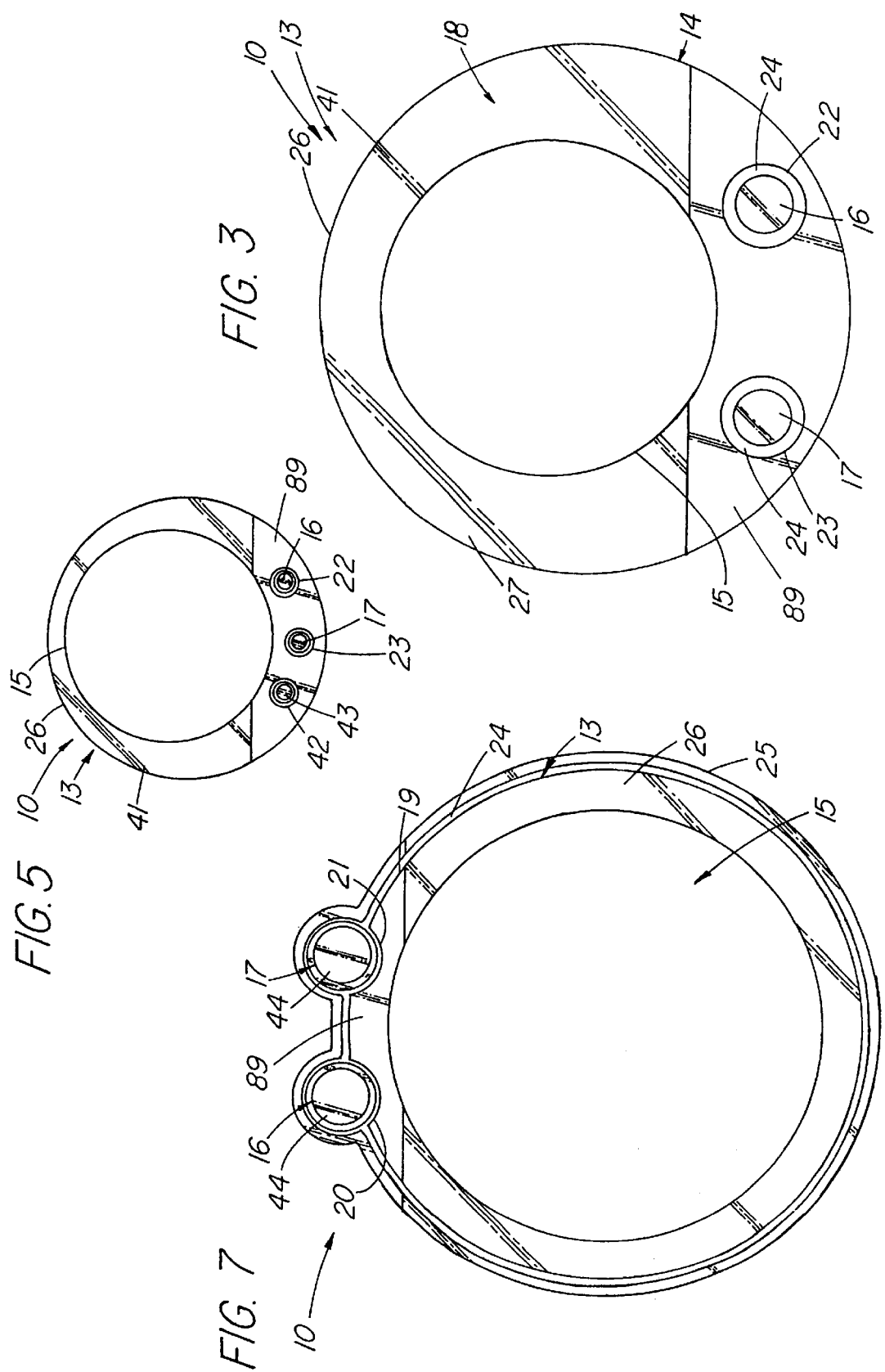

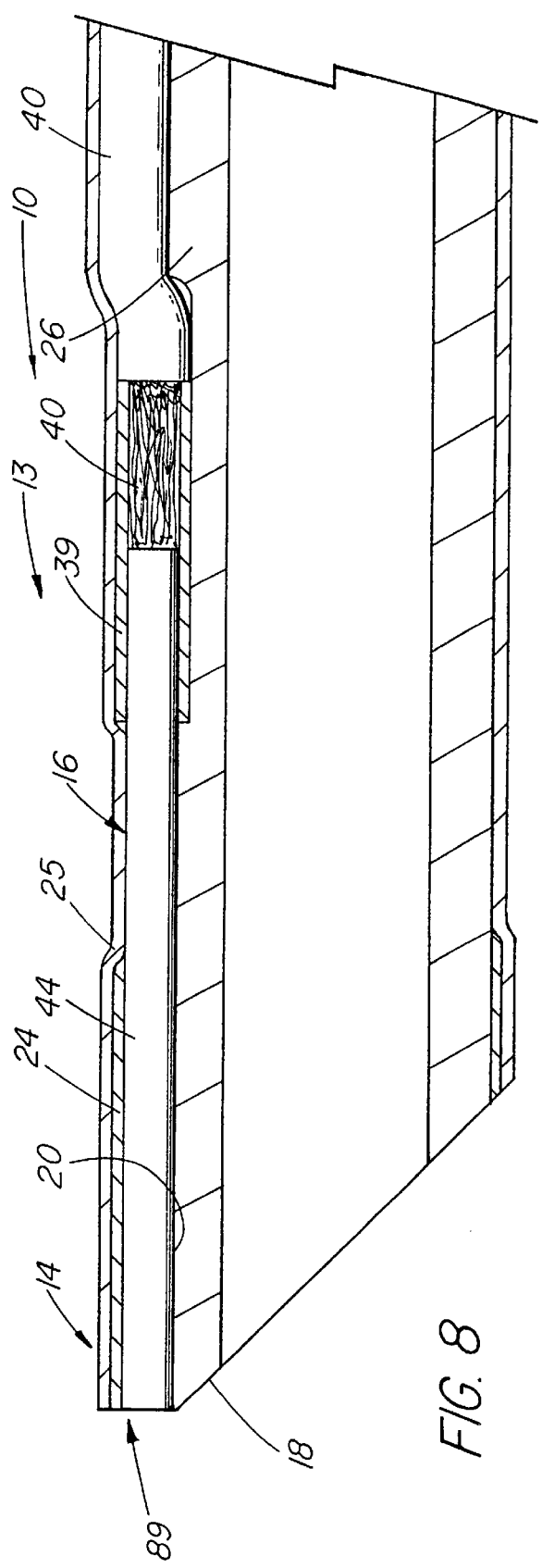
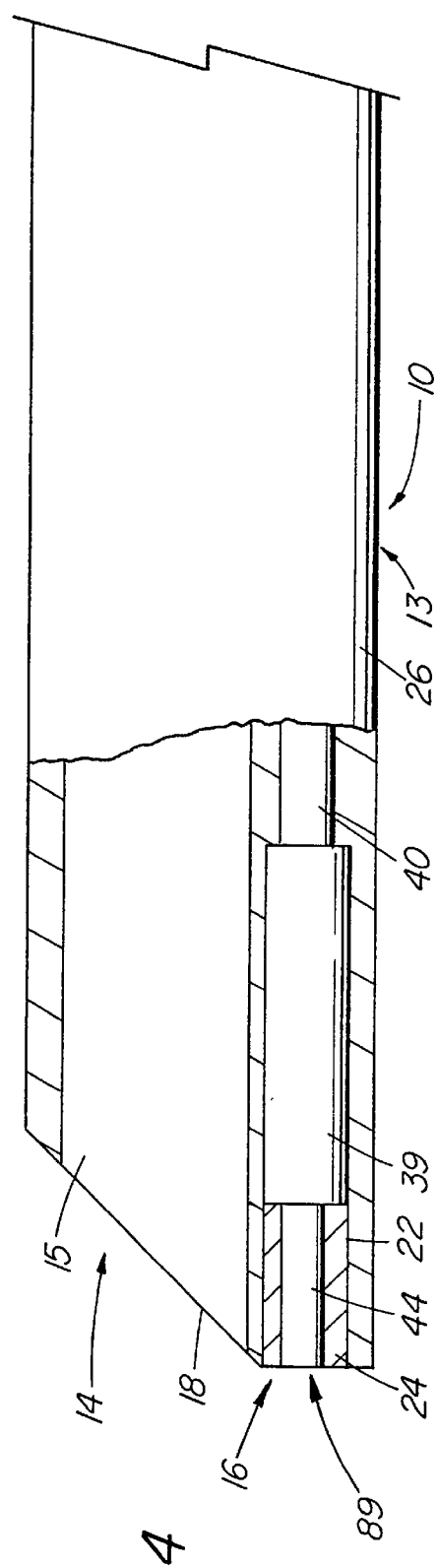
FIG. 8
FIG. 4

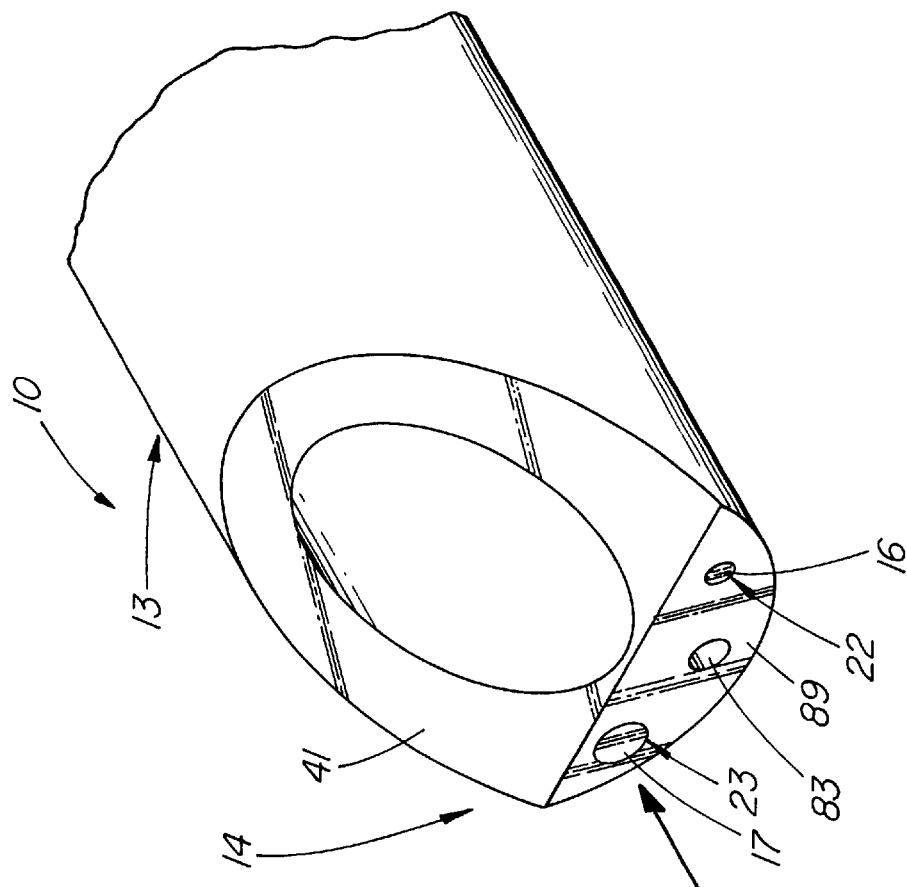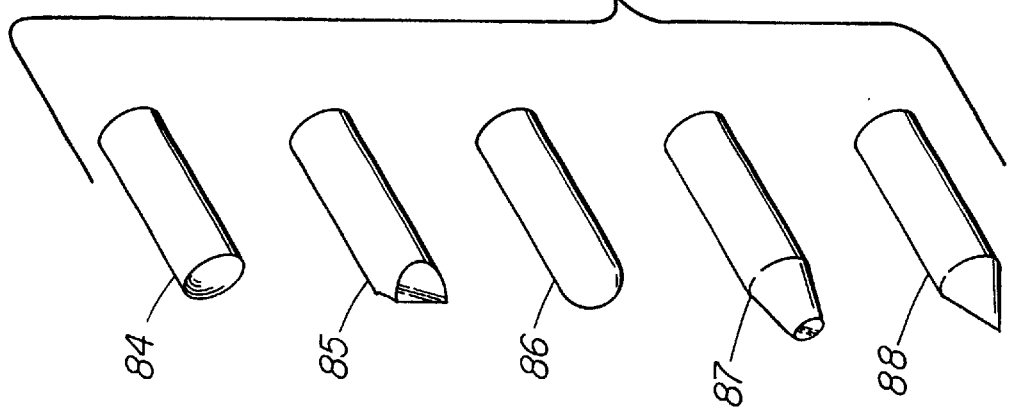
FIG. 14

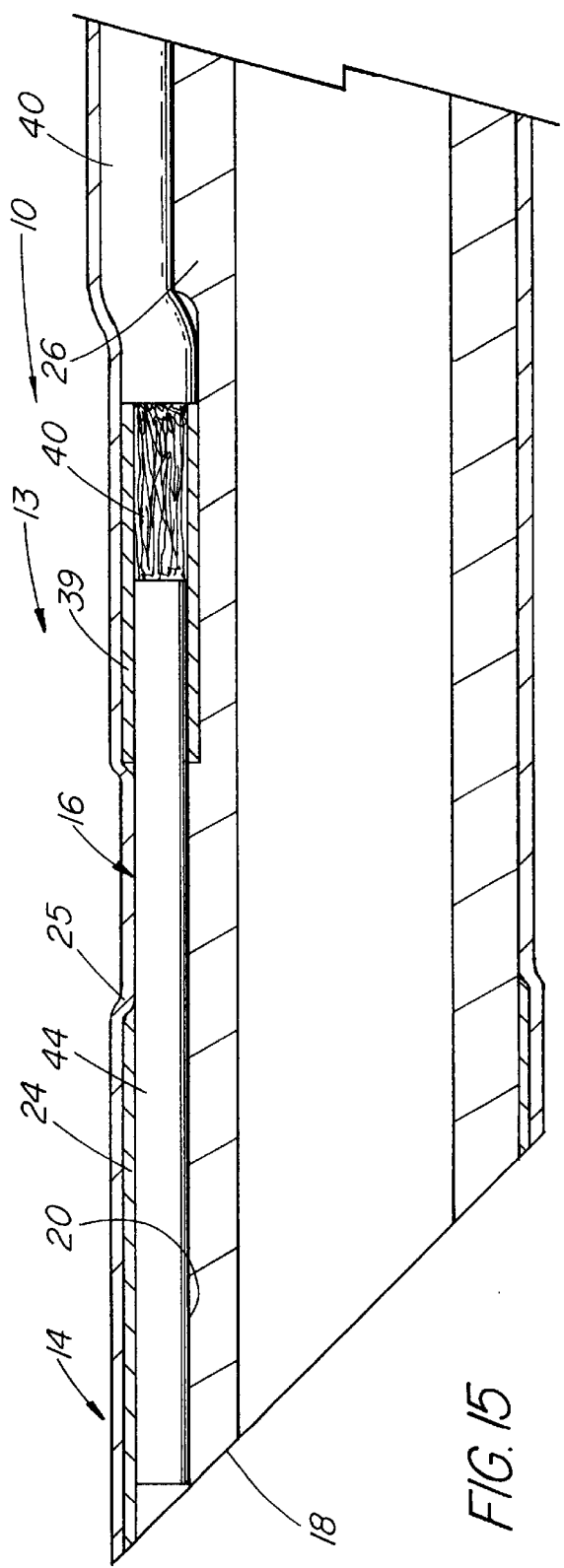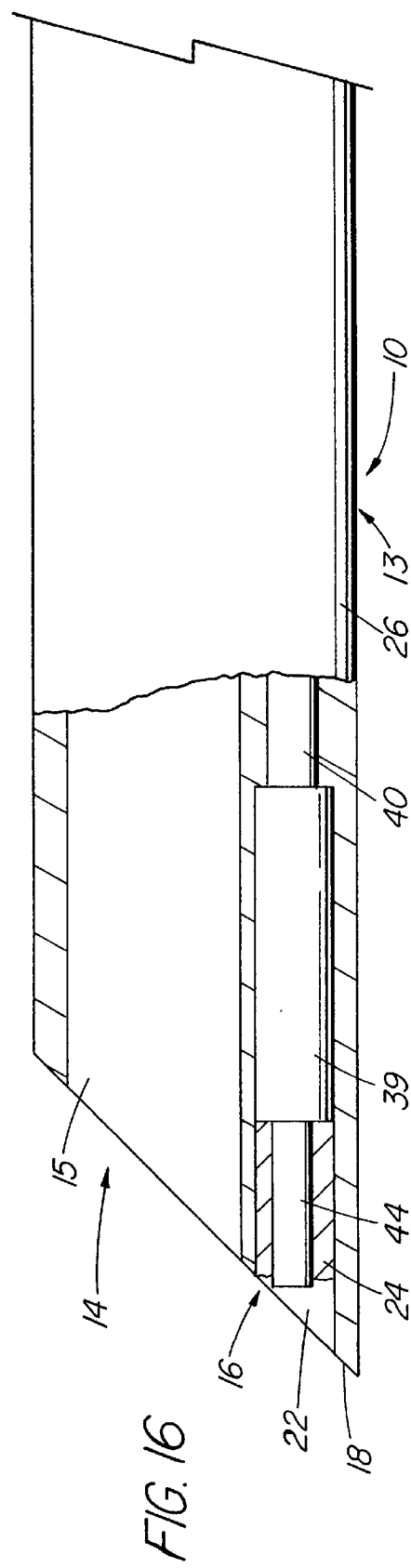

RADIO FREQUENCY DILATOR SHEATH

CROSS-REFERENCE TO RELATED APPLICATIONS

This application claims priority of provisional application Ser. No. 60/031,961 filed Nov. 27, 1996 and provisional application Ser. No. 60/038,521 filed Feb. 26, 1997.

TECHNICAL FIELD

This invention relates generally to medical devices and, in particular, to a dilator sheath using electrical energy to separate encapsulating tissue from an implanted cardiac electrical lead.

BACKGROUND OF THE INVENTION

While cardiac electrical leads typically have a useful life of many years, over time pacemaker and defibrillator leads fail. Unfortunately, by the time they fail, they have become encapsulated by fibrotic tissue against the heart itself or the wall of the vein. Encapsulation is especially encountered in areas where a device has caused tissue injury. Encapsulation is the body's healing response to protect surrounding tissue from further injury. Scar tissue may also form due to continual device-related mechanical stresses (i.e., excessive pressure), infection, or inadequate blood supply to the site. The fibrotic tissue is tough and makes it difficult to remove the lead from the patient without causing trauma to the heart or great vessels. For example, when small diameter veins through which a pacemaker lead passes become occluded with fibrotic tissue, separating the lead from the vein can cause severe damage to the vein such as dissection or perforation.

To avoid this and other possible complications, some useless cardiac leads are simply left in the patient when the pacemaker or defibrillator is removed or replaced. However, such a practice can incur the risk of an undetected lead thrombosis or pulmonary embolism. Such a practice can also impair heart function, as multiple leads can restrict the heart valves through which they pass. Furthermore, such a lead can later become infected.

There are, of course, many other reasons why removal of a useless lead is desirable. For example, if there are too many leads positioned in a vein, the vein can become totally occluded. Multiple leads can be incompatible with one another, interfering with the pacing or defibrillating function. An inoperative lead can migrate during introduction of another adjacent lead, and mechanically induce ventricular arrhythmia. Some recalled leads include J-shaped retention wires that have been known to fracture and protrude through the insulation, causing several reported deaths. Other potentially life-threatening complications can require the removal of the lead as well. For example, removal of an infected pacemaker lead is considered mandatory in the presence of septicemia and endocarditis. Other necessary indications such as pocket infection, chronic draining sinus, and erosion can lead to significant morbidity if the lead is not removed.

Until recently, manual (or direct) traction, weighted (or sustained) traction, and open-heart surgery/thoracotomy have been the most common methods of removing useless or infected cardiac leads. Manual and weighted traction involve the risk of tearing the myocardium and are largely ineffective for leads extensively encased in fibrotic tissue. This procedure is also ineffective in patients with multiple leads when these leads become scarred together at common fibrous binding sites. The risks and trauma associated with an open surgical approach are obvious. Yet another method of transvenously extracting a cardiac lead is by the use of a grasping device, such as a forceps or basket that is positionable around the outer surface of a lead or fragments of a lead. The use of forceps or a basket for lead withdrawal is complicated by the fact that the lead should first be freed from any encapsulating material surrounding it along its path. Furthermore, tearing of the myocardium or vessels can result during attempted extraction. Many of these problems were overcome by the development of a system of tools and methods for transvenous extraction of pacemaker leads and other elongated objects such as catheters. Many of these tools and procedures were developed with the assistance of Cook Pacemaker Corp., Leechburg, Pa., as evidenced by U.S. Pat. Nos. 4,988,347; 5,013,310; 5,011,482; 4,943,289; 5,207,683; 5,507,751; 5,632,749; and corresponding foreign patents. The preferred method involves positioning a lead removal tool or "locking stylet" inside the coiled wire of the lead to engage the coil. Once the locking stylet is positioned inside the coil, reinforcement is provided and extraction forces are concentrated at the lead tip. By using a sheath to apply countertraction at the embedded tip as the lead is extracted, damage to the myocardium can be largely avoided.

Typically, the locking stylet alone does not provide the tensional force required to safely extract the lead due to excessive fibrotic or scar tissue that has encapsulated the lead against the vessel or myocardial wall. Dilator sheaths formed from plastic or metal tubes can be used to disrupt and separate the encapsulating tissue. Commonly, two coaxial dilator sheaths are positioned over the lead and advanced therealong for loosening the lead from the fibrotic tissue on the vein wall. Plastic sheaths are flexible for bending around the natural anatomical curvatures of the vascular system. A problem with the plastic dilator sheaths is that the leading edge of the dilator sheath is weak and can lose its edge and buckle onto the lead during use. As a result, the plastic dilator sheath can become damaged and unusable before the lead is loosened from the fibrotic tissue. Furthermore, the tips of the flexible plastic sheaths can deform when subjected to tough fibrotic tissue. This problem is further heightened when the sheath is bent around a vessel curve. Metal dilator sheaths provide a sharp leading edge for encountering fibrotic tissue. A problem with some metallic dilator sheaths is that they are relatively inflexible and resist bending around natural anatomical curvatures. As a result, a metallic dilator sheath can be difficult or impossible to advance toward the distal end of the pacemaker lead without injuring or obliterating the vein. Flexible metallic dilator sheaths have been developed to address the problems associated with plastic sheaths and rigid metal sheaths. While very effective for their intended use, even metal sheaths are inadequate for the toughest fibrotic tissue and calcification in a vessel. The tensile strength of the fibrous tissue increases with time. Eventually the tissue can even differentiate into cartilage or bone. Attempted separation of difficult fibrotic tissue can cause mechanical trauma to the vessel. Data show that 5.4% of all attempted lead extractions are not successful and 7.5% are only partially successful, almost entirely due to the presence of excessive scar tissue. Lead fragility is another problem and generally escalates over time when a lead has a design flaw or has been structurally compromised.

U.S. Pat. No. 5,423,806 of Dale et al. discloses a laser catheter for ablating encapsulating tissue during the extraction of pacemaker leads. Using directed high energy to burn, desiccate, or melt the tissue encapsulating the lead can reduce the length of the procedure and increase the number of leads that can be extracted. In the practiced embodiment of U.S. Pat. No. 5,423,806, optical fibers are arranged circumferentially around an open lumen through which the lead passes. One problem with this embodiment is that tissue can be readily cored and plug the internal lumen of the device, thus making forward or reverse movement of the device extremely difficult. The laser device is used in combination with a plastic outer sheath and tracks over the lead as the distal tip of the laser burns through any obstructive tissue surrounding the lead. Partly due to the difficulty in visualizing the treatment site, a significant disadvantage of this approach is the risk of burning though the vessel wall or myocardium. This is especially a problem if sufficient tension is not constantly maintained on the lead during the procedure, allowing the distal tip of the laser to angle toward the wall of the vessel or myocardium. This could pose an unacceptable risk for the large number of lead extractions that are elective procedures and do not involve life-threatening indications.

Alternative embodiments of the laser catheter suggested by the Dale reference include having the optical fibers grouped on one side of the catheter or utilizing a single fiber. Either would permit more precise ablation of scar tissue surrounding the lead if the point of ablation can be manipulated and selectively rotated away from the vessel wall. It is suggested that a stylet could be inserted into an additional lumen of the catheter to facilitate rotational control. While providing the physician with control over the point of ablation during the procedure should reduce the risk of accidentally penetrating the vessel wall, the effectiveness of the laser catheter is still limited by the fragility of the optical fibers. Given the tendency of optical fibers to break when subject to lateral bending or rotational forces, current laser catheter designs are not particularly torqueable. An annular arrangement of optical fibers, with its disadvantages, is used that does not require that the catheter be rotated. However, even when merely navigating a laser catheter through a tortuous angle, breakage can occur that can result in the catheter burning through itself or the cardiac lead insulation due to the large amount of heat generated. These disadvantages, along with the much higher cost, limit the laser catheter as an alternative to manual sheaths.

SUMMARY OF THE INVENTION

The foregoing problems are solved and a technical advance is achieved by a medical device for separating an elongated structure such as an electrical cardiac lead implanted in biological tissue. The medical device comprises an inner elongated dilator sheath having a distal end and a passage extending longitudinally therethrough. The medical device further comprises an electrical conductor positioned about the distal end and passage of the inner elongated sheath. The passage of the sheath is sized and configured for placement of an elongated structure, such as an electrical cardiac lead, implanted in biological tissue, such as a vessel leading to or from the heart. When energized, the electrical conductor electrically separates or ablates biological tissue from the elongated structure implanted therein and placed in the passage of the inner dilator sheath. Advantageously, the distal end of the inner elongated dilator sheath is at least partially beveled for mechanically loosening and separating encapsulated tissue from the elongated electrical lead. As a result, the electrical conductor and the mechanical configuration of the inner dilator sheath work in concert with each other to provide separation of extremely tough encapsulating tissue and stubborn calcification deposits from the elongated electrical structure. In addition, the sheath can disrupt the fibrous tissue bands which commonly bind multiple cardiac leads together. The beveled distal end also includes a transverse face that advantageously positions the electrodes of the electrical conductor (therein) so as to establish and maintain an electrical, tissue ablating arc therebetween. The tissue ablating arc also advantageously maintains a necessary gap between the obstructive tissue and the end of electrodes as the dilator sheath is eased forward.

The radio frequency dilator sheath further includes an outer dilator sheath, which also advantageously has a beveled distal end that is coaxially positioned over the inner dilator sheath for providing coordinated longitudinal and rotational movement with the inner dilator sheath for separating encapsulating tissue from an implanted lead.

In the preferred embodiment, first and second electrical conductors are advantageously positioned in the wall of the inner dilator sheath and about the distal end thereof. When connected to a source of radio frequency energy, an electrical arc of radio frequency energy is selectively established between the conductors for heating, cutting, ablating, or melting encapsulating tissue and calcification deposits away from the implanted lead. The electrical conductors preferably have a tungsten electrode tip so as to prevent deterioration of the conductor with an electrical arc emanating therefrom. The electrode tip is conveniently connected via a connector sleeve to a supply conductor which exits the inner dilator sheath about the proximal end thereof.

In another illustrative embodiment, the electrical conductor or conductors are positioned in longitudinal recesses formed in the outer surface of the inner dilator sheath about the distal end thereof. The electrode tip is positioned in the recess and fixedly positioned therein with a biocompatible material, such as a medical grade adhesive or epoxy. An outer wrap, such as a shrink-wrap tube, is positioned around the inner dilator sheath as well as the electrical conductors to fixedly position and mechanically support the remaining portion of the electrical conductors along the remaining length of the inner dilator sheath. As previously suggested, an outer coaxial dilator sheath is also used in combination with this alternative embodiment for separating encapsulating tissue from an implanted elongated structure.

In yet another embodiment of the radio frequency dilator sheath, a plurality of electrical conductors, for example, three, are positioned in the wall of the inner dilator sheath and are selectively energized in pairs or simultaneously to provide further circumferential electrical separation of encapsulated tissue from the implanted lead positioned in the main passage of the dilator sheath.

The inner and outer coaxial dilator sheaths of the present invention each preferably comprises an elongated tubular member of a biocompatible material, the inner sheath having a high temperature resistance or high continuous use temperature preferably over 500° F. In the preferred embodiment, the outer coaxial dilator sheath comprises a polypropylene material, whereas the inner dilator sheath comprises a radiopaque polytetrafluoroethylene material. By way of example, the radiopaque material can include bismuth, barium, bismuth carbonate, platinum, tungsten, or any other commercially available radiopaque material. Other high-temperature resistant biocompatible materials having a heat deflection temperature of, for example, 500° F., include fluorinated ethylene propylene, polyetheretherketone, polyetherimide, polyphenylsulfone, and polyimides.

Preferably, the electrical conductors of the radio frequency dilator sheath include a high temperature electrode tip of a material such as tungsten so as to advantageously prevent deterioration of the conductor due to the electrical arc emanating therefrom during separation of tissue from the implanted structure.

One or more conductors can extend over or in the distal end of the inner sheath. Each conductor can be located on the outer surface, or in a recess on the outer surface, or in a passageway at the distal end region of the inner sheath.

BRIEF DESCRIPTION OF THE DRAWING

FIG. 1 depicts a pictorial view of a preferred embodiment of an illustrative radio frequency dilator sheath of the present invention;

FIG. 2 depicts an enlarged pictorial view of the distal end of the dilator sheath of FIG. 1;

FIG. 3 depicts an enlarged distal-end view of the dilator sheath of FIG. 1;

FIG. 4 depicts an enlarged and partially sectioned side view of the distal end of the dilator sheath of FIG. 1;

FIG. 5 depicts an end view of an alternative embodiment of the dilator sheath of FIG. 1;

FIG. 6 depicts an enlarged pictorial view of another illustrative embodiment of the dilator sheath of FIG. 1;

FIG. 7 depicts an enlarged distal-end view of the dilator sheath of FIG. 6;

FIG. 8 depicts an enlarged and partially sectioned side view of the distal end of the dilator sheath of FIG. 6;

FIG. 13 depicts an enlarged and partially sectioned bottom view of the dilator sheath of FIG. 1 taken along line 13—13;

FIG. 14 depicts an enlarged pictorial view of the distal end of an alternative embodiment of the dilator sheath of FIG. 1;

FIG. 15 depicts an enlarged and partially sectioned side view of the distal end of an alternate embodiment to the dilator sheath of FIG. 1; and FIG. 16 depicts an enlarged and partially sectioned side view of the distal end of an alternate embodiment to the dilator sheath of FIG. 6;

DETAILED DESCRIPTION

Figure 9:
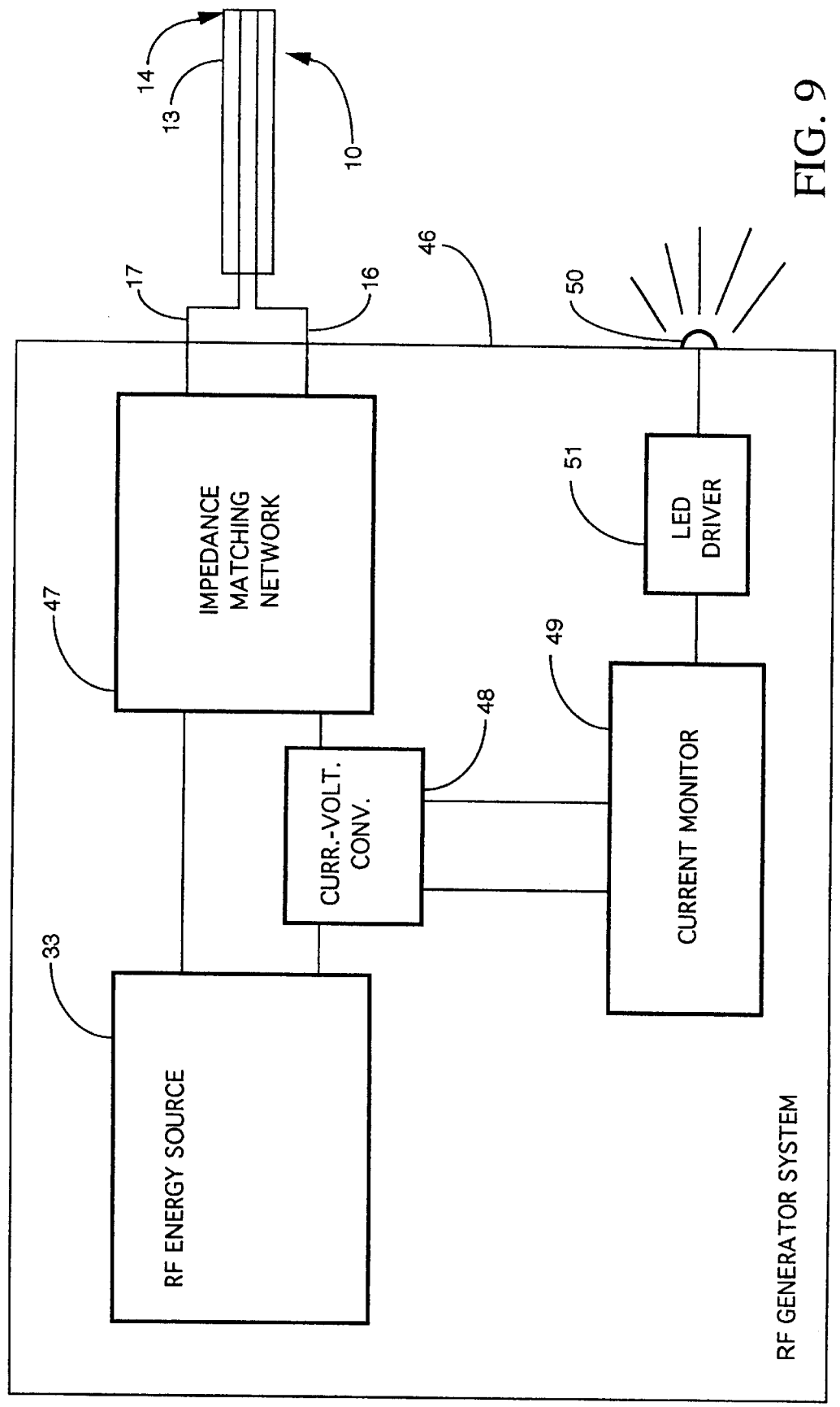
FIG. 9 depicts a block diagram of a radio-frequency generator system connected to the medical device of FIG. 1.

FIG. 1 depicts a pictorial view of a preferred embodiment of an illustrative medical device such as a radio frequency dilator sheath 10 for separating an encapsulated elongated structure such as a cardiac electrical lead 11 from biological tissue 12. Electrical cardiac lead 11 such as from a pacemaker or defibrillator is initially implanted in a blood vessel 30 extending to or from the heart. After a period of time, the elongated structure of the cardiac lead typically becomes encapsulated by fibrotic biological tissue 12 against the wall of the vessel or surrounding tissue. To remove the encapsulated cardiac lead from the vein of a patient, a dilator sheath 10 is used that includes inner and outer coaxial dilator sheaths 13 and 28 that are coaxially positioned over the lead and advanced therealong for mechanically separating the lead from the encapsulating fibrotic tissue 12 on the vessel wall. Inner elongated sheath 13 has a distal end 14 that includes an at least partially beveled distal end 18 for mechanically loosening and separating lead 11 from the encapsulating tissue as the inner sheath is advanced longitudinally back and forth and rotated about the lead as indicated by arrows 34 and 35. Inner elongated dilator sheath 13 also has a passage 15 extending longitudinally therethrough, which is sized and configured for placement therein of elongated structure 11 implanted in vessel 30. Similarly, outer dilator sheath 28 includes a beveled distal end 36 for loosening and separating the encapsulating tissue from the lead with the aid of circular and longitudinal movement as indicated by arrows 37 and 38. Outer dilator sheath 28 also has a passage 29 extending longitudinally therethrough, which is sized and configured for placement therein of inner dilator sheath 13 and elongated electrical structure 11.

Inner and outer coaxial dilator sheaths 13 and 28 are biocompatible material tubes, which are laterally flexible for bending around the natural anatomical curvatures of the vascular system. Although beveled distal ends 18 and 36 of the dilator sheaths provide mechanical separation of the lead from most encapsulating fibrotic tissue, tough fibrotic tissue or calcification deposits present a significant problem for separation and often cause damage to the leading edge of these beveled distal ends. As a result, medical device 10 also includes at least one electrical conductor such as a bipolar pair of electrical conductors 16 and 17 that are positioned about distal end 14 and passage 15 of inner elongated dilator sheath 13. This electrical conductor pair extends longitudinally along the inner elongated sheath and exits therefrom about proximal end 31 of the sheath. The exiting of electrical conductors 16 and 17 about proximal end 31 of the inner sheath is mechanically supported by hollow plastic handle 45 that is provided to facilitate manipulation of the dilator sheath. The handle that is comprised of two cupped parts 45' and 45" can be made from a wide variety of polymers, including commercially available polyamides (nylon), acetal, or acrylonitrile butadiene styrene (ABS). The handle also provides physical protection for the connection of the supply conductor wires 40 to the remaining proximal end wires of the electrical conductors 16 and 17. The corresponding wires are each joined with solder and further secured with short pieces of heat shrink tubing 80. The electrical conductors 16 and 17 are secured to the handle with an adhesive such as silicon where they exit therefrom.

FIG. 13 depicts an enlarged and partially sectioned bottom view of the dilator sheath of FIG. 1 along the line 13—13. Within the hollow plastic handle 45, the supply conductor wires 40 exit the sheath 13 through a pair of longitudinally offset ports 81 and 82 that communicate with respective first and second electrical conductor passages 22 and 23 within the sheath wall 41.

Returning to FIG. 1, electrical conductors 16 and 17 proximally terminate in an electrical connector 32, which connects to a commercially available source 33 of radio frequency energy. Radio frequency energy is selectively applied to at least one electrical conductor, which can be either unipolar or bipolar, and delivered to distal end 14 of the inner dilator sheath. An arc of electrical energy is established at the distal end of the inner sheath between electrical conductors 16 and 17 and separates, ablates, melts, or cuts encapsulating tissue 12 or calcification deposits from the cardiac electrical lead. As a result, the delivery of radio frequency energy to the distal end of the inner elongated dilator sheath is used singly or in combination with the mechanical configuration of the inner and outer coaxial sheaths to separate encapsulating biological tissue 12 from implanted electrical cardiac lead 11.

FIG. 9 depicts a block diagram of radio-frequency generator system 46 connected to medical device 10 of FIG. 1 via electrical conductors 16 and 17. The radio-frequency generator system includes a commercially available source 33 of radio-frequency energy connected to dilator sheath 10 via well-known impedance matching network 47. Electrical conductors 16 and 17 extend longitudinally through elongated inner sheath 13 and terminate at distal end 14 thereof for establishing an arc of electrical energy therebetween. Electrical conductors 16 and 17 have a real impedance of approximately 2000 Ohms. Typically, commercially available radio-frequency energy sources have an output impedance of approximately 100 Ohms. Impedance matching network 47 matches the different impedances of the electrical dilator sheath conductors 16 and 17 to that of the radio-frequency energy source 33. The impedance matching network minimizes power loss between the dilator sheath and energy source and permits monitoring of the current and voltage applied to the dilator sheath when an arc of electrical energy has been established between the electrical conductors at the distal end of the dilator sheath. To monitor the various levels of current and voltage applied to dilator sheath 10, a well-known current-to-voltage converter 48 is positioned in the radio frequency generator system between impedance matching network 47 and energy source 33, as shown. The radio frequency current flowing between the impedance matching network and the energy source through current-to-voltage convertor 48 is transformed to generate a voltage signal representative of the current flowing to the dilator sheath. This voltage signal is applied to current monitor 49, which then applies a signal to indicator lamp 50 via well-known LED driver circuit 51. Current monitor 49 is set to detect the amount of current flowing to dilator sheath 10. When an arc of electrical energy is established between electrical conductors 16 and 17 at the end of dilator sheath 10, a relatively large amount of radio frequency current flows in the conductors. This large amount of current is indicative of when the dilator sheath is ablating or cutting encapsulating tissue. As a result, the level of this current is monitored and the current monitor 49 adjusted to light indicator lamp 50 when an arc of electrical energy is established between the electrical conductors. This visual indication signals the attending physician that ablation of encapsulating tissue is occurring. This signal is in addition to the tactile feel of the dilator sheath as it is advanced along the implanted cardiac lead.

When an arc is not established between the distal ends of electrical conductors 16 and 17, the amount of current flowing in dilator sheath 10 as well as radio-frequency generator system 46 is much less. The current monitor detects the drop in current and extinguishes indicator lamp 50.

Figure 10:
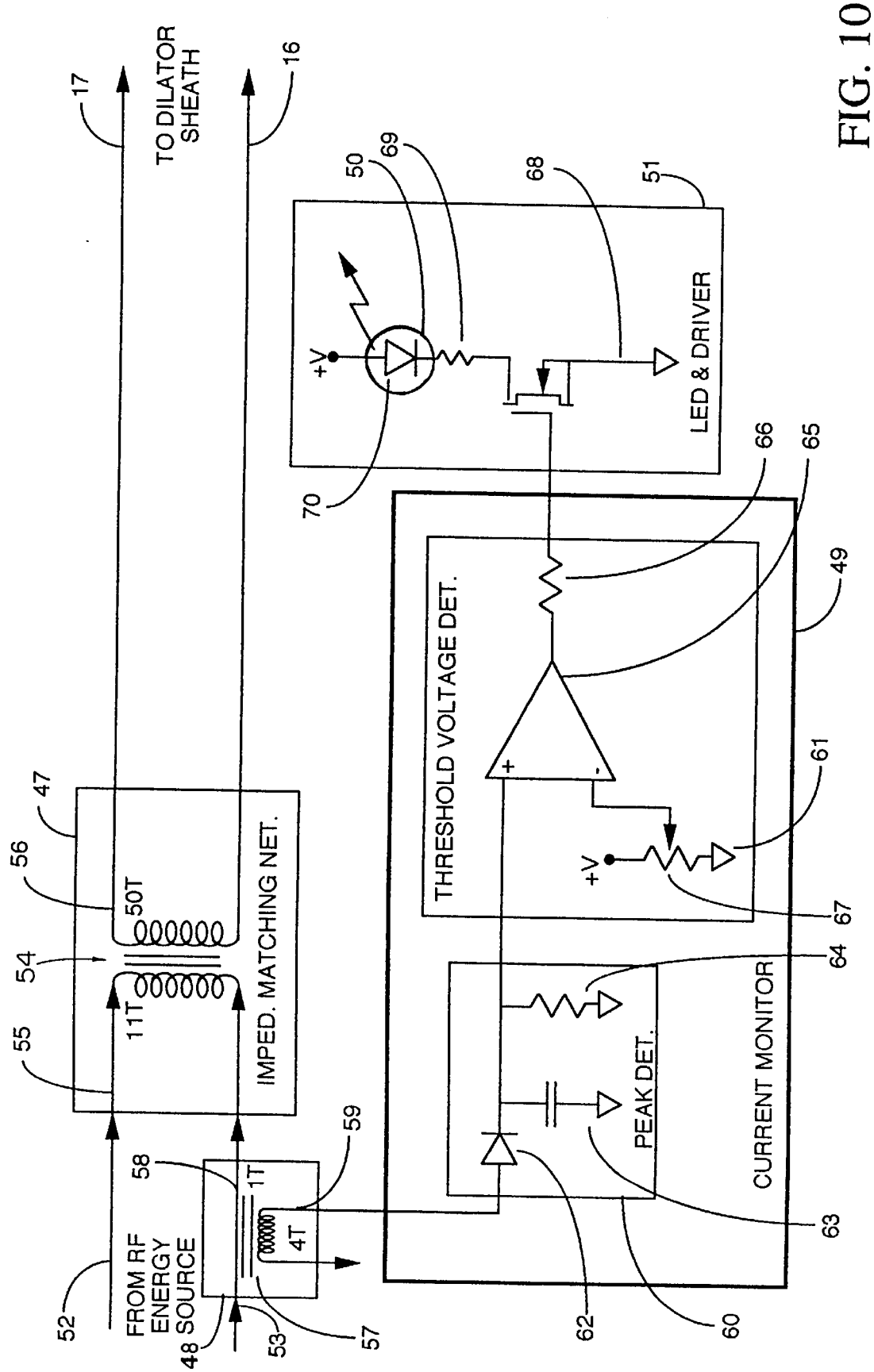
FIG. 10 is a schematic diagram of the radio-frequency generator system of FIG. 9.

FIG. 10 is a schematic diagram of impedance matching network 47, current-to-voltage converter 48, current monitor 49, and LED indicator lamp 50 and driver circuit 51 therefor. Impedance matching network 47 includes a well-known radio-frequency transformer 54 using ferrite toroid cores, such as F240-77 cores, which are commercially available from Amidon Inc., Anaheim, Calif. Primary winding 55 of the transformer includes approximately 11 turns of wire connected to conductors 52 and 53 from energy source 33. Secondary winding 56 of the transformer is approximately 50 turns of wire connected to electrical conductors 16 and 17 of the dilator sheath. This provides a turns ratio of approximately 4.5:1, which will match the 100 Ohm impedance of the energy source to the 2000 Ohm impedance of the dilator sheath with minimal power loss. As is well known, the voltage and current is transformed between the primary and secondary windings of the transformer in a 4.5:1 ratio. The impedance ratio is transformed per the square of the turns ratio, such as 20:1, which matches the impedance of the two devices.

Current-to-voltage converter 48 is connected to primary winding 55 of radio-frequency transformer 54 between radio-frequency energy source 33 and impedance matching network 47. Current-to-voltage converter 48 includes a radio-frequency transformer 57 having a ferrite toroid core commercially designated F50-61, which is also available from the Amidon Corporation. The primary winding 58 of this transformer is one turn, whereas the secondary winding 59 is a four-turn winding. This 4:1 turns ratio is to convert the large current flowing through the primary winding to a voltage signal that is applied to current monitor 49.

Current monitor 49 is connected to the single, secondary winding turn of transformer 57 and includes peak detector 60 connected in series to threshold voltage detector 61. Both of these circuits are well known electrical circuits. Peak detector 60 includes diode 62, such as commercially available diode IN914 connected in series to the input of threshold voltage detector 61. Connected in parallel to the output of diode 62 are capacitor 63 of, for example, 0.05 µf, and load resistor 64 of, for example, 6.8M Ohms.

Threshold voltage detector 61 includes a comparator 65, such as commercially available operational amplifier CA3160E, connected in series through load resister 66 of, for example, 100K Ohms, to the input of LED and driver circuit 51. One input of the comparator is connected to peak detector 60, whereas the other input of the comparator is connected to a voltage divider potentiometer 67, such as a 20K Ohm, ten-turn potentiometer connected between ground and a 9 volt source. The dilator sheath is connected to the energy source and energized to cause an arc of electrical energy to be conducted between conductors 16 and 17 at the distal end of the dilator sheath. The potentiometer of the threshold voltage detector circuit is adjusted to cause indicator lamp 50 to light, indicating that an electrical arc has been established. The dilator sheath is then put in contact with the tissue to cause the arc to extinguish. Should the indicator lamp still be lit, the potentiometer is again adjusted to extinguish the indicator lamp.

LED and driver circuit 51 includes well-known FET switch 68, such as commercially available VN2222, which is connected in series between load resistor 69 of, for example, 1K Ohms, and light emitting diode 70. The output of the threshold voltage detector turns the switch on and off, permitting current to flow through the light emitting diode 70, causing indicator lamp 50 to light and extinguish as previously described.

Figure 12:
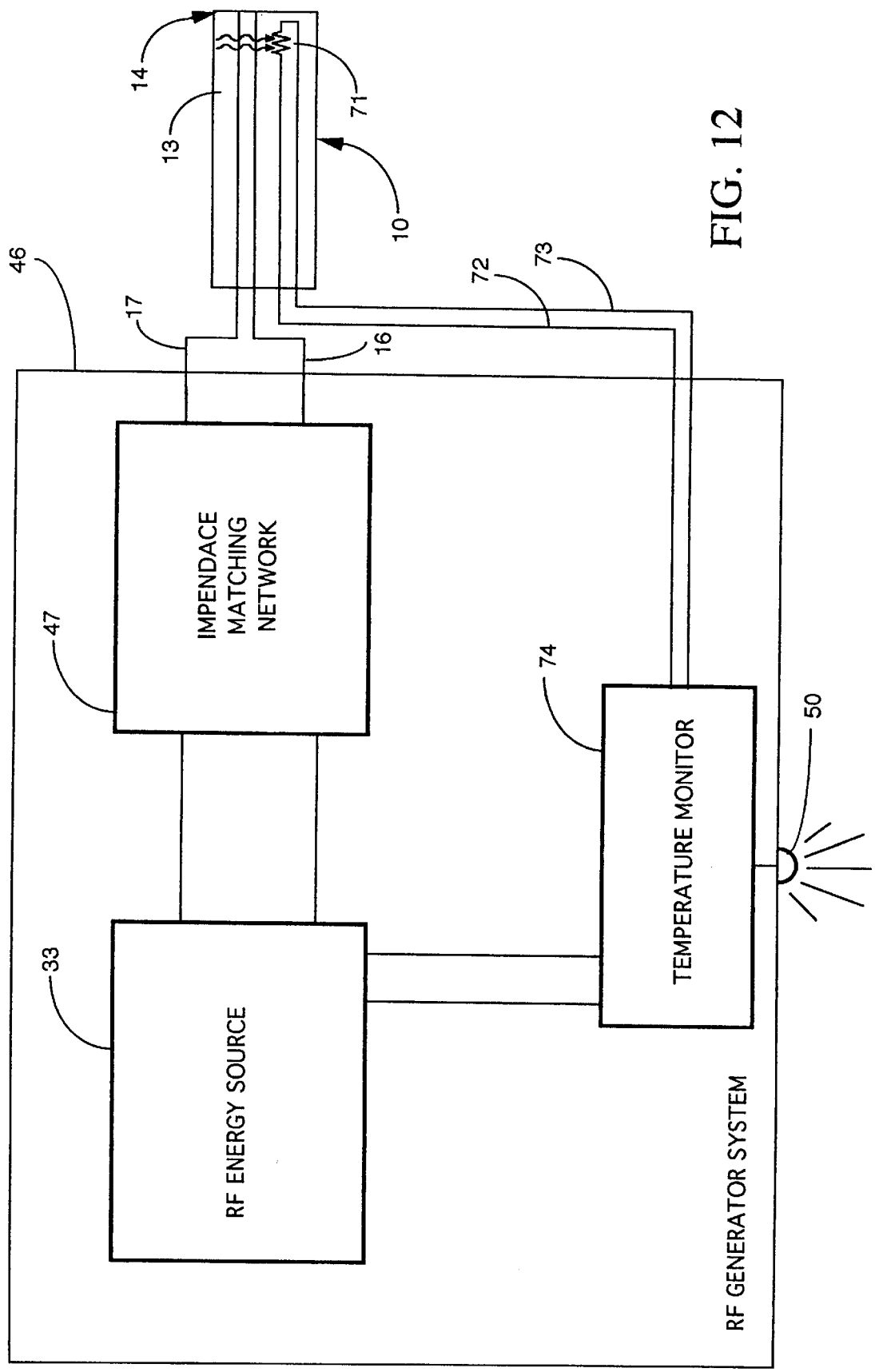
FIG. 12 depicts a block diagram of yet another embodiment of a radio-frequency generator system connected to the medical device of FIG. 1.

FIG. 12 depicts another embodiment of radio-frequency generator system 46 connected to dilator sheath 10 of FIG. 1. In this embodiment, dilator sheath 10 includes a temperature sensor 71, such as a commercially available thermistor, positioned at distal end 14 of the dilator sheath adjacent the distal ends of conductors 16 and 17. This thermistor and electrical conductors 72 and 73 are longitudinally positioned through the dilator sheath in a manner similar to those of electrical conductors 16 and 17. When an arc of radio-frequency electrical energy is established between electrical conductors 16 and 17, thereby separating, ablating, melting, or cutting encapsulating tissue, heat is generated by the electrical arc and the severed tissue. The heat generated by the electrical arc and the severed tissue is sensed by temperature sensor 71, which transmits an electrical signal indicative thereof to radio-frequency generator system 46. Alternatively, or in combination with thermal sensor 71, an optical fiber or other sensing device can be positioned at distal end 14 of dilator sheath 10. These additional or alternative sensors are used to monitor or indicate when an electrical arc has been established between conductors 16 and 17 for dissecting or removing encapsulating tissue from the encapsulated lead.

RF generator system 46 includes radio-frequency energy source 33 that is connected to dilator sheath 10 through impedance matching network 47. Impedance matching network 47 includes components as previously described. Generator system 46 also includes a temperature monitor circuit 74 which is connected to thermal sensor 71 via conductors 72 and 73. Temperature monitor circuit 74 is a well-known circuit for lighting and extinguishing indicator lamp 50, as previously discussed, and for indicating the presence and absence of an electrical arc between dilator sheath conductors 16 and 17. Temperature monitor circuit 74 can also be used to provide feedback to radio-frequency energy source 33 to regulate the amount of energy applied to dilator sheath 10.

Figure 11:
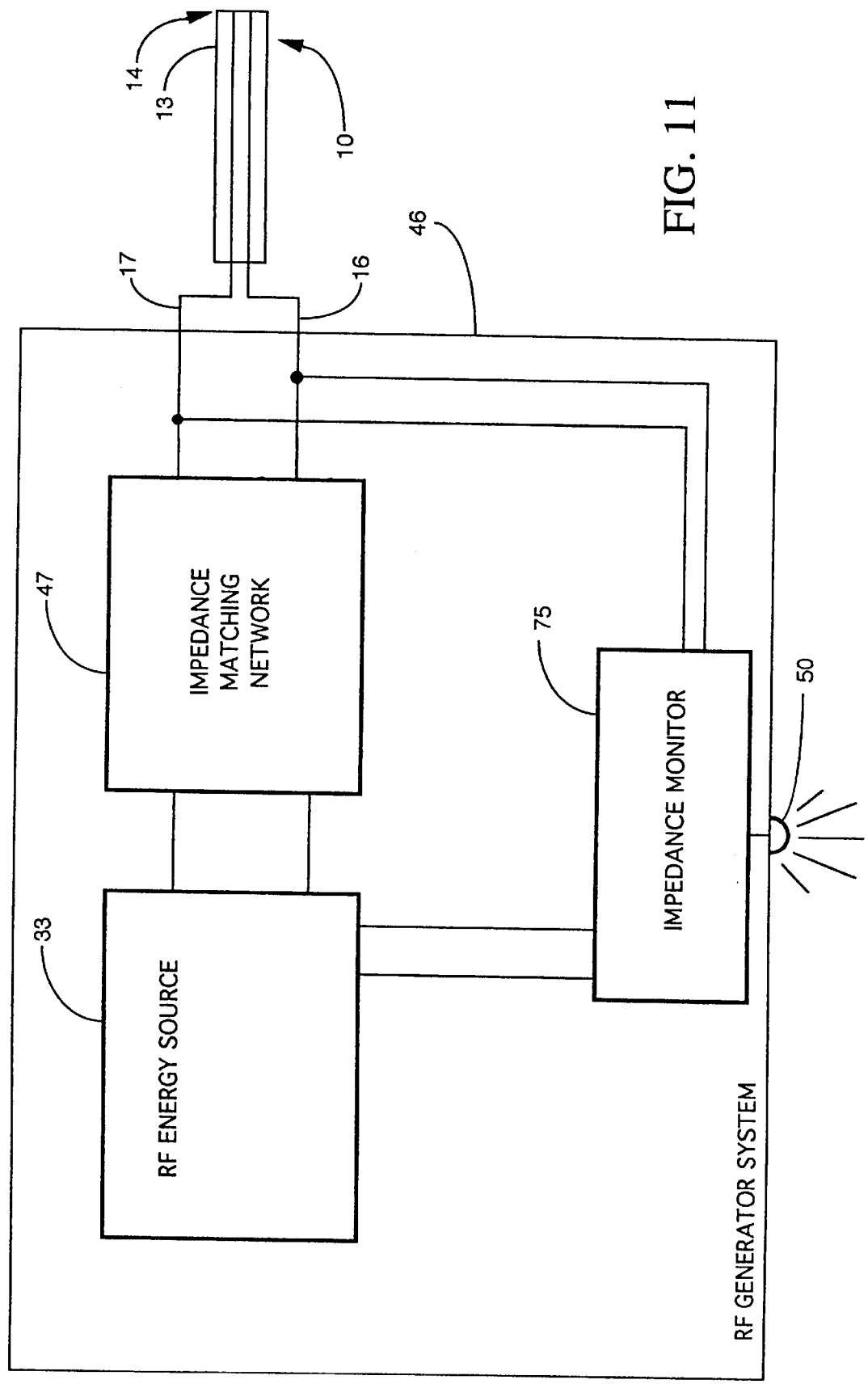
FIG. 11 depicts a block diagram of still another embodiment of a radio-frequency generator system connected to the medical device of FIG. 1.

FIG. 11 depicts still another embodiment of radio-frequency generator system 46 connected to dilator sheath 10 of FIG. 1. Electrical conductors 16 and 17 extend to distal end 14 of inner elongated dilator sheath 13. In this particular embodiment, generator system 46 includes radio-frequency energy source 33 connected to dilator sheath 10 via impedance matching network 47 as previously described. Impedance monitor circuit 75 is connected across the output of impedance matching network 47 to detect changes in impedance of the dilator sheath due to the presence and absence of an electrical arc between electrical conductors 16 and 17 at distal end 14 of the sheath. As previously suggested, the differences in impedance detected by impedance monitor 75 are used to energize and extinguish indicator lamp 50 during the presence and absence of the electrical arc at the distal end 14 of the dilator sheath. In addition, the impedance monitor circuit can be connected to radio-frequency energy source 33 to provide a feedback signal thereto for regulating the amount of energy applied to the dilator sheath in a well-known manner.

In addition, it is contemplated that radio-frequency energy source 33 can be controlled with impedance monitor 75, temperature monitor 74, or current monitor 49 to provide a large pulse of electrical energy to the distal end of the dilator sheath. This large pulse of electrical energy is applied via electrical conductors 16 and 17 so as to cause the tissue fluids about the encapsulated lead to enter a gaseous state, thereby essentially exploding the tissue away from the encapsulated lead.

FIG. 2 depicts an enlarged pictorial view of distal end 14 of inner dilator sheath 13 of medical device 10 of FIG. 1. FIG. 3 depicts an enlarged distal end view of inner dilator sheath 13 of medical device 10 of FIG. 1. The inner elongated dilator sheath 13 is configured in the form of an elongated tubular member 26 with main passage 15 extending longitudinally therethrough. However, the inner dilator sheath and its main passage can take on any cross-sectional shape such as square, rectangular, elliptical, triangular, etc., or any combination thereof. As previously indicated, main passage 15 is sized and configured for placement therein of the elongated structure of the electrical cardiac lead. Also included in tubular member 26 is first and second electrical conductor passages 22 and 23 also extending longitudinally in wall 41 of the tubular member. Electrical conductor passages 22 and 23 have respective electrical conductors 16 and 17 fixedly positioned therein, with the aid of biocompatible material 24 such as a commercially available medical grade adhesive or epoxy. One example of medical grade epoxy is Hysol® epoxy, which is available from the Dexter Corp., Olean, N.Y. Tubular member 26 of inner dilator sheath 13 is formed from a high temperature biocompatible polymer material which is capable of withstanding the temperatures resulting from the generation of an electrical arc between electrical conductors 16 and 17. Preferably, tubular member 26 of inner dilator sheath 13 comprises polytetrafluoroethylene (PTFE), which is radiopaque due to the addition of a radiopaque material 27 such as, for example, bismuth, barium, bismuth carbonate, platinum, tungsten, or any other commercially available radiopaque material. As is well known, PTFE is also a lubricious material. Other high temperature resistant biocompatible materials having a heat deflection temperature in excess of, for example, 500° F. and suitable for the tubular member of dilator sheath 13 include fluorinated ethylene propylene (FEP), polyetheretherketone (PEEK), polyetherimide (PEI), polyphenylsulfone (PPS), and polyimides. The use of other biocompatible material having lower heat deflection temperatures is also contemplated depending on the particular application and the heat generated by the electrical conductors. Should lubricity become a concern with any of the biocompatible materials, a hydrophillic coating can be applied to the surface thereof.

By way of example, tubular member 26 of inner dilator sheath 13 is approximately 19 inches long and has an outer diameter of approximately 0.155 inches with a main passage inner diameter of approximately 0.113 inches. Wall 41 of tubular member 26 has a minimum outer wall thickness of approximately 0.021 inches. Electric cardiac leads typically have an outer diameter of approximately 0.100 inches, which is readily accommodated by the diameter of main passage 15 of the sheath. The diameter of main passage 15 can be readily adapted to facilitate the removal of electric cardiac leads as small as 0.060 inches and as large as 0.125 inches. The diameter of the main passage is selected so to provide a clearance of no more than 0.020 inches. This tolerance minimizes, if not eliminates, the collection of tissue inside the dilator sheath, which can block up the main passage thereof. Electrical conductor passages 22 and 23 are formed in the thicker portion of wall 41 with a diameter of approximately 0.022 inches. Outer dilator sheath preferably comprises a polypropylene material and is approximately 13 inches long with an outside diameter of 0.233 inches and an inside diameter of 0.208 inches. Beveled distal ends 18 and 36 form a 45° angle with respect to the longitudinal axis of sheaths 13 and 28. Beveled distal edge 18 of the inner dilator sheath 13 is truncated to form a transverse face 89 whereby the electrical conductors 16 and 17 are flush with the distal edge of the sheath. The transverse face is formed with the electrical conductors extending out from beyond the distal end of the sheath and then cutting the distal portion of the distal beveled edge with a diamond saw such that the transverse face or surface 89 is perpendicular to the longitudinal axis of the sheath.

FIG. 4 depicts an enlarged and partially sectioned side view of distal end 14 of inner dilator sheath 13 of medical device 10 of FIG. 1. As depicted, the distal end of electrical conductor passages 22 and 23 are counterbored to a diameter of approximately 0.030 inches and to a depth of approximately 0.3 inches. Electrical conductors 16 and 17 each include an electrode tip 44 of a high temperature electrical conductor material such as, for example, tungsten for generating a radio frequency electrical arc therefrom. Electrical conductor 16 also includes connector sleeve 39 of, for example, stainless steel, which is connected to a low resistance electrical conductor 40 of, for example, No. 2840/7 stranded and twisted copper wire available from the Alpha Wire Company, Elizabeth, N.J. Electrical connector sleeve 39 is approximately 0.2 inches long with an inner diameter of approximately 0.021 inches and an outer diameter of 0.028 inches. Tungsten electrode tip 44 is approximately 0.2 inches long with a diameter of approximately 0.020 inches. Half of the electrode tip is positioned in connector sleeve 39. The tungsten electrode tip is formed from a pure tungsten wire such as used with TIG welding electrodes, which are commercially available from any welding supply shop. The connector sleeve is mechanically crimped to the tungsten tip and electrical supply conductor 40. Electrical conductor 16 is first positioned through conductor passage 22 and exits at or in the vicinity of the proximal end of the tubular member. The connector sleeve and tungsten electrode tip are then pulled into the counterbored portion of the conductor passage and fixedly positioned therein with biocompatible material 24 such as a medical grade adhesive or epoxy as previously indicated.

As depicted in FIGS. 2 and 3, electrical conductors 16 and 17 are positioned in conductor passages 22 and 23, respectively, in the thicker portion of wall 41 of tubular member 26. Center-to-center spacing of the electrical conductors and conductor passages is preferably in the range of 0.090 to 0.100 inches with a maximum spacing of 0.150 inches and a minimum spacing of 0.010 inches.

FIG. 5 depicts an end view of an alternative embodiment of medical device 10 of FIG. 1 in which inner dilator sheath 13 includes at least three electrical conductor passages extending through wall 41 of tubular member 26. These three conductor passages include previously described conductor passages 22 and 23 along with conductor passage 42 for positioning electrical conductors 16, 17 and 43 therein, respectively. As previously described, inner sheath passage 15 is utilized for positioning the electrical cardiac lead therein. In operation, an electrical arc is established between central conductor 17 and outer conductor 16 or, alternatively, between central conductor 17 and outer conductor 43, either simultaneously or alternatively with the other conductor pair. The electrical arcs established therebetween are used to establish a broader base of radio frequency energy for the separation of tissue from the electrical cardiac lead. It is also contemplated that electrical conductors be positioned entirely around the circumference of the inner dilator sheath.

FIG. 6 depicts an enlarged pictorial view of another illustrative embodiment of inner dilator sheath 13 of medical device 10 of FIG. 1. In particular, this embodiment of inner dilator sheath 13 positions electrical conductors 16 and 17 in outer surface 19 thereof. FIG. 7 depicts an enlarged distal end view of inner dilator sheath 13 of medical device 10 of FIG. 6. To fix the relative position of electrical conductors 16 and 17 in the outer surface of the dilator sheath, recesses 20 and 21 are formed in outer surface 19. Electrical conductors 16 and 17 are positioned in respective outer surface recesses 20 and 21 and fixedly positioned therein with biocompatible material 24 such as a medical grade adhesive or epoxy, as previously described. The biocompatible adhesive or epoxy is applied over the electrical conductors and around the circumference of the dilator sheath just about the distal end thereof. To fixedly position the remaining portion of electrical conductors 16 and 17 with respect to dilator sheath 13, outer wrap 25 is positioned around the electrical conductors and elongated tubular member 26.

As previously indicated, inner elongated dilator sheath 13 is configured in the form of an elongated tubular member 26 with main passage 15 extending longitudinally therethrough. Furthermore, electrical conductors 16 and 17 each include a tungsten electrode tip 44, a connector sleeve 39 and a supply conductor 40. In this particular embodiment, the length of the tungsten tip is increased to approximately 0.75 inches with the diameter of recesses 20 and 21 being maintained at approximately 0.022 inches. The proximal end of the recesses are enlarged to accommodate connector sleeve 39. Outer wrap 25 is preferably a high temperature shrink-wrap tube of a KYNAR® material available from Pennwalt Corp., Philadelphia, Pa. This shrink-wrap tube preferably has an inner diameter of 0.187 inches with a wall thickness of 0.005 inches and is heated to shrink around the conductors and inner dilator sheath 13. This shrink-wrap material shrinks about the inner dilator sheath with temperatures in the range of 450° F. to 500° F. The outer wrap tube 25 provides mechanical strength to electrical conductors 16 and 17 so as to minimize breakage or movement during separation of tissue from the electrical cardiac lead. The center-to-center spacing of electrical conductor 16 and 17 is maintained as previously described with respect to the first embodiment.

FIG. 8 depicts an enlarged and partially sectioned side view of distal end 14 of inner dilator sheath 13 of medical device 10 of FIG. 6. As depicted, electrical conductor 16 includes electrode tip 44 and supply conductor 40 interconnected by connector sleeve 39. Electrode tip 44 is positioned in recess 20 and fixedly positioned therein with biocompatible material 24 and outer wrap tube 25. Distal end 14 includes beveled distal end 18 which makes an angle of approximately 45 degrees with respect to the longitudinal axis of the dilator sheath with a transverse face 89 at the distal tip perpendicular to the longitudinal axis of the dilator sheath. This beveled distal end is formed after the electrical conductors, biocompatible material, and outer wrap tube are positioned around tubular member 26. The transverse face is formed using a diamond saw to remove the most distal portion of the beveled distal end such that electrical conductors 16 and 17 are flush with the distal end of the sheath.

FIG. 14 depicts an enlarged pictorial view of the distal end of an alternative embodiment of the dilator sheath of FIG. 1. In this embodiment, a third lumen 83 formed in wall 41 of sheath 13 through which dye or other fluid or material can be injected or aspirated. Also depicted is an alternative embodiment in which electrical conductors 16 and 17 are of different diameters. Still further depicted, are alternative embodiments of electrode tip 44 such as conductor tips 84–88 which provide selected examples of alternative tip shapes that can be used including concave 84, chisel 85, rounded 86, truncated 87 and conical 88. These tips can either be slightly protruding, flush, or slightly recessed with respect to distal transverse face 89 of the distal end 14 of the dilator sheath. If the electrical conductor tips are protruding or recessed too much, there can be difficulty in establishing or maintaining an electrical arc for cutting. The method of placing the specially shaped conductor tips 84–88 is the same as in the preferred embodiment except that the transverse face 89 is created prior to threading the supply conductor wires 40 into the first and second electrical conductor passages 22,23.

FIGS. 15 and 16 depict enlarged and partially sectioned side views of the distal end of an alternate embodiment of the dilator sheath of FIGS. 1 and 6, respectively. In each of these embodiments, the beveled distal end 18 is not truncated distally as in the preferred embodiment, forming a transverse face or surface such that the electrical conductors are flush with the distal end. In these alternate embodiments, each electrode tip 44 is slightly recessed from the face of the beveled distal end 18 which terminates at a sharp edge extending distal to the electrode tips. The sharp beveled edge can be used advantageously to mechanically disrupt scar tissue along the path of the lead, thus complimenting the action of the radio frequency energy.

In operation, electrical conductors 16 and 17 are connected to a commercially available source of radio-frequency energy commonly found in hospitals, such as the Model Force FX RF Generator available from Valleylab, Boulder, Colo. This electrosurgical unit (ESU) is capable of delivering approximately 50 to 100 Watts of power with a radio-frequency fundamental of approximately 500 KHz (500 KHz±10 KHz) modulated by 120 Hz (65% 120 Hz modulation) to the tungsten electrode tips. The radio-frequency dilator sheath 10 of FIG. 15 was tested with a similar Valleylab generator (Model SSE2L) on an anesthetized sheep with the heart exposed through the right side of the ribs. With a setting of 2 on the electrosurgical generator, connective tissue was cut with 100 mA. Also at a setting of 2, muscle outside the rib cage was cut with 80–100 mA. The electrosurgical generator was then set to 2.5 to cut a fat pad on the outside of the pericardium without any stimulation of the heart. The heart could be stimulated through the pericardium at this setting. The next set of cuts were performed by placing the dilator sheath on the exterior surface of the right ventricle. The data obtained is shown in Table A, below.

TABLE A

Electrical Characteristics of Bipolar Sheath Cutting the Ventricular Surface

| ESU Knob Setting | Current (mA) | Voltage (Vrms) | Power (Watts) | Impedance ('Ω) |
|---|---|---|---|---|
| 2.5 | 180 | 360 | 65 | 2000 |
| 3 | 160 | 520 | 83 | 3250 |
| 4.5 | 190 | 580 | 110 | 3050 |
| 5 | 205 | 540 | 111 | 2630 |

All of these cuts caused stimulation of runs of ventricularly-based ectopic beats; however, no fibrillation occurred.

In another sheep, the sheath was used intravascularly to remove an atrial lead implanted 6 months; scar tissue was freed by electrosurgical dissection in the superior vena cava and atrium. In a third sheep, scar tissue along a coronary sinus lead implanted 12 months was freed by electrosurgical dissection in combination with sheath rotation within the coronary sinus. Injection of contrast media confirmed integrity of the vessel after extraction. No complications arose from the use of the electrosurgical dissection sheath.

As a result of these animal experiments, the dilator sheath of this invention demonstrated its separation of encapsulating tissue from an electrical cardiac lead positioned in the vessel leading to the heart. The impedance of the radio frequency dilator sheath needs to be approximately 100 ohms so as to match the impedance of most commercially available electrosurgical units. A well-known impedance matching transformer or circuit as previously described can be used to match the impedance of the electrical conductors to that of the electrosurgical unit.

It is to be understood that the above-described radio frequency dilator sheath is merely an illustrative embodiment of the principles of this invention and that other dilator sheaths may be devised by those skilled in the art without departing from the spirit and scope of this invention. In particular, the dilator sheaths have been described as being comprised of a high temperature resistant polymer or copolymer plastic material. However, any temperature resistant material is contemplated and can include combinations of dilator sheaths made of a metal or a combination of metal and plastic material. The shape or configuration of the dilator sheaths can be accommodated for any elongated structure shape and/or the vessel or tissue in which the elongated structure is implanted. Furthermore, the outer dilator sheath can be withdrawn from the proximal end of the inner dilator sheath as long as the electrical conductors are positioned so as not to interfere with its removal. In particular, the conductor passages can extend throughout the entire length of the dilator sheath, thus allowing the electrical conductors to exit through the wall of the dilator sheath at its proximal end. The electrical conductor connector would also have to be removable or small enough so as to facilitate placement through the passage of the outer sheath. Otherwise, it is contemplated that the outer coaxial dilator sheath is positioned over the inner sheath from the distal end thereof. As previously suggested, the radio frequency dilator sheath of this invention is preferably of a bipolar configuration; however, a unipolar construction is fully contemplated with an electrical return path established through the patient and exterior to the surface of the patient. It is also contemplated that an additional lumen can be included in the inner dilator sheath to inject contrast media or medicaments into the vessel or tissue.

What is claimed is:

1. A medical device (10) for separating an elongated structure (11) implanted in biological tissue (12), comprising:
    an elongated sheath (13) having a distal end (14) and a passage (15) extending longitudinally therethrough, said passage being sized and configured for placement of an elongated structure (11) implanted in biological tissue (12), and said passage having an inside diameter of no more than about 0.15 inches; and
    an electrical conductor (16) positioned about said distal end and said passage of said elongated sheath, whereby said electrical conductor when energized separates biological tissue from an elongated structure implanted therein and placed in said passage of said elongated sheath.

2. The medical device of claim 1 further comprising another electrical conductor (17) positioned about said distal end and said passage of said elongated sheath.

3. The medical device of claim 1 wherein said distal end of said elongated sheath comprises a beveled distal end (18).

4. The medical device of claim 1 wherein said electrical conductor is also positioned in an outer surface (19) of said elongated sheath.

5. The medical device of claim 1 wherein said elongated sheath has an other passage (22) extending longitudinally therein; and wherein said electrical conductor is also positioned in said other passage of said elongated sheath.

6. The medical device of claim 5 further comprising a biocompatible material (24) fixedly positioning said electrical conductor in said other passage of said elongated sheath.

7. The medical device of claim 1 wherein said elongated sheath comprises an elongated tubular member (26).

8. The medical device of claim 7 wherein said elongated tubular member includes a radiopaque material (27) and is laterally flexible.

9. A medical device (10) for separating an elongated structure (11) implanted in biological tissue (12), comprising:

an elongated sheath (13) having a distal end (14) and a passage (15) extending longitudinally therethrough, said passage being sized and configured for placement of an elongated structure (11) implanted in biological tissue (12); and an electrical conductor (16) positioned about said distal end and said passage of said elongated sheath, whereby said electrical conductor when energized separates biological tissue from an elongated structure implanted therein and placed in said passage of said elongated sheath;

wherein said distal end of said elongated sheath comprises a beveled distal end (18); and wherein said beveled distal end (18) is truncated to form a transverse surface (89) being approximately perpendicular to a longitudinal axis of said elongated sheath (13), and wherein said electrical conductors are (a) at least in, (b) particularly in, or (c) about said distal end adjacent to said transverse surface.

10. A medical device (10) for separating an elongated structure (11) implanted in biological tissue (12), comprising:

an elongated sheath (13) having a distal end (14) and a passage (15) extending longitudinally therethrough, said passage being sized and configured for placement of an elongated structure (11) implanted in biological tissue (12); and an electrical conductor (16) positioned about said distal end and said passage of said elongated sheath, where by said electrical conductor when energized separates biological tissue from an elongated structure implanted therein and placed in said passage of said elongated sheath;

wherein said electrical conductor is also positioned in an outer surface (19) of said elongated sheath; and wherein said outer surface of said elongated sheath includes a recess (20) therein and extending longitudinally therealong and wherein said electrical conductor is also positioned in said recess.

11. The medical device of claim 10 further comprising another electrical conductor (17) positioned about said distal end and said passage of said elongated sheath; wherein said outer surface of said elongated sheath includes an other recess (21) therein and extending longitudinally therealong; and wherein said other electrical conductor is also positioned in said other recess.

12. The medical device of claim 11 further comprising a biocompatible material (24) fixedly positioning said electrical conductor in said recess and said other electrical conductor in said other recess and on said outer surface of said elongated sheath.

13. The medical device of claim 12 further comprising an outer wrap (25) positioned around said elongated sheath and said electrical conductor and said other electrical conductor.

14. The medical device of claim 10 further comprising a biocompatible material (24) fixedly positioning said electrical conductor in said recess and on said outer surface of said elongated sheath.

15. The medical device of claim 14 further comprising an outer wrap (25) positioned around said elongated sheath and said electrical conductor.

16. A medical device (10) for separating an elongated structure (11) implanted in biological tissue (12), comprising:

an elongated sheath (13) having a distal end (14) and a passage (15) extending longitudinally therethrough, said passage being sized and configured for placement of an elongated structure (11) implanted in biological tissue (12); and an electrical conductor (16) positioned about said distal end and said passage of said elongated sheath, whereby said electrical conductor when energized separates biological tissue from an elongated structure implanted therein and placed in said passage of said elongated sheath;

wherein said elongated sheath has another passage (22) extending longitudinally therein; and wherein said electrical conductor is also positioned in said other passage of said elongated sheath; and wherein the medical device further comprises another electrical conductor (17) positioned about said distal end and said passage of said elongated sheath; wherein said elongated sheath has yet another passage (23) extending longitudinally therein; and wherein said other electrical conductor is also positioned in yet said other passage of said elongated sheath.

17. The medical device of claim 16 further comprising a biocompatible material (24) fixedly positioning said electrical conductor in said other passage and said other electrical conductor in yet said other passage of said elongated sheath.

18. A medical device (10) for separating an elongated structure (11) implanted in biological tissue (12), comprising:

an elongated sheath (13) having a distal end (14) and a passage (15) extending longitudinally therethrough, said passage being sized and configured for placement of an elongated structure (11) implanted in biological tissue (12); and an electrical conductor (16) positioned about said distal end and said passage of said elongated sheath, whereby said electrical conductor when energized separates biological tissue from an elongated structure implanted therein and placed in said passage of said elongated sheath;

further comprising another elongated sheath (28) having a passage (29) sized and configured for placement of said elongated sheath therethrough.

19. A medical device (10) for separating an elongated structure (11) implanted in biological tissue (12), comprising:

an elongated sheath (13) having a beveled distal end (18) and a passage (15) extending longitudinally therethrough, said beveled distal end being truncated and forming a transverse surface (89), said passage being sized and configured for placement of the elongated structure (11); and an electrical conductor (16) positioned about said transverse surface and said passage, whereby said electrical conductor when energized separates biological tissue from the elongated structure.

* * * * *